United States Patent
Luo et al.

(10) Patent No.: US 10,669,500 B2
(45) Date of Patent: Jun. 2, 2020

(54) COATING COMPOSITIONS COMPRISING ADHESION PROMOTING BASE LAYER

(71) Applicants: JMEDTECH (XIAMEN) COATING TECHNOLOGY CO. LTD, Xiamen (CN); JMEDTECH COATING TECHNOLOGIES PTE LTD, Singapore (SG)

(72) Inventors: Jingnan Luo, Singapore (SG); Honglei Wang, Singapore (SG)

(73) Assignees: JMEDTECH (XIAMEN) COATING TECHNOLOGY CO. LTD, Xiamen (CN); JMEDTECH COATING TECHNOLOGIES PTE LTD, Singapore (SG)

( * ) Notice: Subject to any disclaimer, the term of this patent is extended or adjusted under 35 U.S.C. 154(b) by 205 days.

(21) Appl. No.: 15/580,885

(22) PCT Filed: Jun. 8, 2016

(86) PCT No.: PCT/SG2016/050266
§ 371 (c)(1),
(2) Date: Dec. 8, 2017

(87) PCT Pub. No.: WO2016/200337
PCT Pub. Date: Dec. 15, 2016

(65) Prior Publication Data
US 2018/0163152 A1    Jun. 14, 2018

(30) Foreign Application Priority Data
Jun. 8, 2015 (GB) .................... 1509919.5

(51) Int. Cl.
| | |
|---|---|
| *C08F 2/48* | (2006.01) |
| *C08F 2/46* | (2006.01) |
| *C08G 61/04* | (2006.01) |
| *C10M 107/28* | (2006.01) |
| *C09D 171/02* | (2006.01) |
| *A61L 29/14* | (2006.01) |
| *A61L 29/08* | (2006.01) |
| *C09D 4/06* | (2006.01) |
| *C09D 187/00* | (2006.01) |
| *C08F 290/06* | (2006.01) |
| *C09D 5/00* | (2006.01) |
| *C09D 129/14* | (2006.01) |
| *C10M 177/00* | (2006.01) |
| *B05D 3/06* | (2006.01) |
| *C10N 70/00* | (2006.01) |

(52) U.S. Cl.
CPC ......... *C10M 107/28* (2013.01); *A61L 29/085* (2013.01); *A61L 29/14* (2013.01); *C08F 290/061* (2013.01); *C09D 4/06* (2013.01); *C09D 5/002* (2013.01); *C09D 129/14* (2013.01); *C09D 171/02* (2013.01); *C09D 187/005* (2013.01); *C10M 177/00* (2013.01); *A61L 2400/10* (2013.01); *B05D 3/067* (2013.01); *C10M 2209/0845* (2013.01); *C10N 2070/00* (2013.01); *C10N 2240/66* (2013.01)

(58) Field of Classification Search
CPC .............. C10M 107/28; C10M 177/00; C10N 2070/00; C09D 171/02; C09D 129/14; C09D 5/002; A61L 29/14
USPC ........................................ 427/508, 487, 457
See application file for complete search history.

(56) References Cited

U.S. PATENT DOCUMENTS

| | | | |
|---|---|---|---|
| 2002/0013549 A1 | 1/2002 | Zhong et al. | |
| 2003/0060783 A1* | 3/2003 | Koole ................... | A61L 29/085 604/265 |
| 2004/0143180 A1 | 7/2004 | Zhong et al. | |
| 2006/0165999 A1 | 7/2006 | Fansler et al. | |
| 2011/0144579 A1 | 6/2011 | Elton | |
| 2012/0077049 A1 | 3/2012 | Lin | |
| 2013/0136847 A1 | 5/2013 | Lee et al. | |
| 2014/0193474 A1 | 7/2014 | Babcock et al. | |

(Continued)

FOREIGN PATENT DOCUMENTS

| | | |
|---|---|---|
| CN | 104307051 A | 1/2015 |
| WO | 9938546 A1 | 8/1999 |
| WO | 2000078884 A1 | 12/2000 |

(Continued)

OTHER PUBLICATIONS

International Search Report and Written Opinion issued in PCT/SG2016/050266, dated Aug. 31, 2016.

(Continued)

*Primary Examiner* — Jessica Whiteley
(74) *Attorney, Agent, or Firm* — Patterson + Sheridan, LLP

(57) ABSTRACT

Described herein are coatings and formulations thereof for coating a substrate for use in producing a lubricious coating on a substrate surface that is to be inserted into the body lumen of a subject. Said coatings all contain an adhesion promoting coating formulation for applying to a substrate material that is formed from a polymeric adhesion promoter, a monomeric or polymeric crosslinking agent and a photoinitiator, where the polymeric adhesion promoter is a block copolymer comprising hydrophobic hydrophilic polymer blocks and/or a hydrophilic polymer comprising hydrophilic functional groups, where from 10% to 100% of the hydrophilic functional groups are capped with a hydrophobic functional group and the formulations thereof further contain a solvent to enable the coating to be applied to a substrate surface.

23 Claims, 3 Drawing Sheets

(56) References Cited

U.S. PATENT DOCUMENTS

2014/0220337 A1   8/2014   Nguyen et al.

FOREIGN PATENT DOCUMENTS

| WO | 2002085963 A2 | 10/2002 |
| WO | 2005025633 A1 | 3/2005 |
| WO | 2007065722 A1 | 6/2007 |
| WO | 2008104573 A2 | 9/2008 |
| WO | 2009/117345 A2 | 9/2009 |

OTHER PUBLICATIONS

United Kingdom Search Report dated Sep. 9, 2015 for Application No. GB1509919.5.
European Search Report in related application 16807928.3 dated Dec. 20, 2018.

* cited by examiner

COATING COMPOSITIONS COMPRISING ADHESION PROMOTING BASE LAYER

FIELD OF INVENTION

The present invention relates to the whole or part of a coating for the surface of an article that enables easier insertion and/or removal of the article from a body lumen of a subject.

BACKGROUND

The listing or discussion of a prior-published document in this specification should not necessarily be taken as an acknowledgement that the document is part of the state of the art or is common general knowledge.

Lubricious coatings are designed to provide medical devices with a slippery surface, which enhances the comfort of a subject during insertion, placement and/or removal of the medical device. This is because a lubricious coating reduces the insertion force and allows the medical device to traverse the tissue/body lumen it is inserted into more easily. Such coatings also avoid severe abrasion between the surface of the device and the tissues/body lumen of the subject. Typical medical devices that are coated with a lubricious coating include guidewires, catheters and other medical devices that are required to be inserted into a subject (and potentially removed thereafter).

In general, such lubricious coatings may contain a single layer or two layers—a top layer and a bottom layer. The top layer generally contains a hydrophilic polymer and is intended to come into direct contact with the tissues and/or body lumen of a subject. The bottom layer is intended to provide improved adhesion between the top layer and the surface of the medical device. The majority of effort in this field has focused on providing improved top layers/single layer formulations, as this is what comes into direct contact with the subject. International patent application publication Nos. WO 2007/065722, and WO 2008/104573 disclose the use of a polyelectrolyte material as part of a layer intended to be in direct contact with a lumen of a subject. International patent application publication No. WO 2011/157805 discloses the use of a Norrish type II photoinitiator comprising substituted benzophenone, xanthone, tioxanthone or anthraquinone as part of a similar layer.

International patent application publication No. WO 2008/104572 discloses the use of a supporting polymer backbone with reactive moieties that can capture a hydrophilic polymer coating layer. The problem with this design is that when the coated medical devices are inserted into human body, the entrapped hydrophilic polymer layer has a tendency to rub off due to abrasion, resulting in a high level of particulate/migrable matter in the lumen of the subject, which is undesirable. Hence, one of the main challenges being faced by the industry is to reduce the release of particulate/migrateable matter from lubricious coatings on a medical device following insertion into a subject. The particulates formed from the polymer/coating material may be dangerous to human body in some application, such as angioplasty and stent placement, due to their ability to migrate and, in some cases, aggregate.

While the top (i.e. functional) layer provides lubricity, the base layer of a two layer coating is intended to ensure the stability of the coating. However, there is a broad range of materials used in medical devices that need to be coated to ensure hydrophilic lubricious performance of the device. These medical device materials include, but are not limited to, metals, polyurethane (PU), polyvinyl chloride (PVC), latex, pebax, nylon, polypropylene, polyethylene (HDPE and LDPE), fluorinated ethylene propylene (FEP), poly (ethene-co-tetrafluoroethene) (ETFE), poly(ethylene terephthalate) (PET) and silicone elastomers etc, all of which are potential substrates for a lubricious coating. Some of these materials are very hydrophobic (low surface energy), such as PP (polypropylene), HDPE, FEP and ETFE. To achieve a stable hydrophilic coating on these very hydrophobic materials remains challenging. International patent application publication Nos. WO 2011/157805 and WO 2008/031596 only use PVC and PU as the substrate materials, and none of the exemplified coatings have sufficient adhesion to substrates such as silicone, PP, FEP and the like. Further, the exemplified coatings on such materials have poor adherence and durability and are relatively easy to rub off from the substrate surface when the entire device (including coating) has been wetted. It is possible to improve the adhesion of a hydrophobic substrate and a hydrophilic coating layer using pretreatments, such as solvents, plasma and harsh chemical solutions. These pretreatments attempt to reduce the surface free energy of the substrate, so that a hydrophilic coating solution can spontaneously spread on it. However, the use of pretreatments increases the manufacturing cost and reduces the efficiency of manufacturing.

Therefore, there remains a need to: (1) develop a coating with negligible release of particulates/migrateables from the top coat of a two-layer coating; and (2) develop a versatile base coat platform to be directly applied on different substrates to achieve robust adhesion between substrate and lubricous functional layer. It is possible that solving (2) may result in the improvement of (1).

SUMMARY OF INVENTION

In a first aspect of the invention, there is provided an adhesion promoting coating formulation for applying to a substrate material, comprising:
  a polymeric adhesion promoter;
  a first monomeric or polymeric crosslinking agent;
  a photoinitiator; and
  a solvent, wherein
  the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group.

In a second aspect of the invention, there is provided a adhesion promoting coating for forming a base coating layer on a substrate material onto which a lubricious top layer coating can be formed, comprising:
  a polymeric adhesion promoter;
  a first crosslinked polymeric matrix formed by a first monomeric or polymeric crosslinking agent, wherein
  the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group.

In embodiments of the first and second aspects of the invention:
  (a) the polymeric adhesion promoter may be a block copolymer,
  the hydrophilic block may be chosen from one or more of the group selected from polysaccharide (such as chitosan), poly(vinyl alcohol) (PVA), polymethacrylic acid, poly (ethylene glycol) (PEG), polyacrylamide (PAM), poly(2-oxazoline), and polyethylenimine (PEI), and the hydrophobic block may be chosen from one or more of the group selected from polystyrene (PS), polybutadiene (PB), polyisoprene (PI), poly(methyl methacrylate) (PMMA), poly(methylacrylate) (PMA), poly(propylene oxide) (PPO), poly(hydroxyethylmethacrylate) (PHEMA), poly(vinyl ether) (PVE), poly(vinyl methyl ether) (PVME), poly(vinyl butyl ether) (PVBE), polyimide and poly(dimethylsiloxane) (PDMS), poly(N-isopropylacrylamide) (PNIPAM) (e.g. the hydrophilic block may be chosen from poly (ethylene glycol) (PEG) and the hydrophobic block is chosen from poly(propylene oxide) (PPO));

(b) when the polymeric adhesion promoter is a hydrophilic polymer comprising hydrophilic functional groups, where from 10% to 100% of the hydrophilic functional groups are capped with a hydrophobic functional group, the hydrophilic polymer comprising hydrophilic functional groups may be one or more of the group selected from polyethylenimine (PEI), polyacrylamide (PAM), polysaccharide, and poly(vinyl alcohol) (PVA), and the hydrophobic functional group may cap one or two hydrophilic functional groups and is selected from one or more of methylene ($CH_2$), methyl ($CH_3$), ethylene ($CHCH_3$), ethyl ($CH_2CH_3$), $C_{3-6}$ alkyl, and $C_{3-6}$ alkylene (e.g. $CH(CH_2)_2CH_3$), where the latter two groups are unsubstituted or substituted by a hydroxyl group (e.g. the hydrophilic polymer comprising hydrophilic functional groups is poly(vinyl alcohol) (PVA), and the hydrophobic functional group caps two hydroxyl groups and is $CH(CH_2)_2CH_3$);

(c) from 25% to 100% (e.g. from 30% to 100%, such as from 35% to 100%, from 50% to 75% or from 30% to 50%) of the hydrophilic functional groups may be capped with a hydrophobic functional group;

(d) the polymeric adhesion promoter may have a number average molecular weight of from 20,000 to 2,000,000 and/or is linear, branched or crosslinked;

(e) the first monomeric or polymeric crosslinking agent may be a monomer or polymer with at least two functional groups capable of crosslinking (for example each of the at least two functional groups are selected from the group consisting of acrylate and methacrylate; and/or when the first monomeric or polymeric crosslinking agent is a polymer, the polymer is a polyester or polyether);

(f) the first monomeric or polymeric crosslinking agent may be selected from the group consisting of butanediol dimethacrylate, bisphenol diacrylate, tricyclodecane dimethanol diacrylate, pentaerythritol triacrylate, epoxy acrylate/methacrylate oligomer, polyester acrylate/methacrylate oligomer, and acrylic acrylate oligomer, optionally wherein the first monomeric or polymeric crosslinking agent is selected from the group consisting of bisphenol A epoxy acrylate, bisphenol diacrylate, tripropylene glycol diacrylate, propoxylated neopentyl diacrylate, butanediol dimethacrylate, tricyclodecane dimethanol diacrylate, ethoxylated bisphenol A diacrylate, bisphenol A ethoxylate dimethacrylate, propoxylated glycerol diacrylate, pentaerythritol triacrylate, ditrimethylolpropane tetraacrylate, dipentaerythritol pentaacrylate, dipentaerythritol penta/hexaacrylate, tripropylene diacrylate, trimethylol propane ethoxylate triacrylate, trimethylol propane propoxylate triacrylate, di(trimethylolpropane) tetraacrylate, glycerol propoxylate triacrylate, pentaerythritol propoxylate triacrylate, poly(ethylene glycol) diacrylate, poly (propylene glycol) diacrylate, and tri(propylene glycol) diacrylate;

(g) the first monomeric or polymeric crosslinking agent may be a polyether with at least two curable acrylate and/or methacrylate groups;

(h) the first monomeric or polymeric crosslinking agent may have a molecular weight of from 200 to 50,000 Daltons (e.g. from 200 to 10,000 Daltons, from 400 to 5,000 Daltons, such as from 400 to 2,000 Daltons).

In embodiments of the first aspect of the invention:

the polymeric adhesion promoter may be present in an amount of from 0.05 wt % to 10 wt % (e.g. from 0.1 wt % to 5 wt %);

the first monomeric or polymeric crosslinking agent may be present in an amount of from 0.2 wt % to 7 wt %;

the photoinitiator may be present in an amount of from 0.01 wt % to 2 wt %; and the solvent may be present in an amount of from 92 wt % to 99 wt %, (e.g. the hydrophilic and/or hydrophobic polymer is present in an amount of from 0.1 wt % to 5 wt %, the first monomeric or polymeric crosslinking agent is present in an amount of from 0.6 wt % to 5 wt %, the photoinitiator is present in an amount of from 0.1 wt % to 1 wt %, and the solvent is present in an amount of from 94 wt % to 98 wt %).

When used herein, the term "oligomer" may refer to a compound having a repeating unit of two to ten and is considered to be a subset of the term "polymer".

In a third aspect of the invention, there is provided a kit of parts for forming a lubricious coating on a substrate surface in need thereof, said coating comprising an adhesion promoting coating layer directly on the surface of the substrate and a lubricious coating layer on the adhesion promoting coating layer, the kit comprising:

(a) an adhesion promoting coating formulation as described in the first aspect of the invention or in any technically sensible combination of its embodiments; and (b) a lubricious coating formulation comprising:
    a solvent;
    an initiator; and
    at least one hydrophilic curable polymer having at least two curable functional groups or at least one hydrophilic curable polymer with at least one curable functional group and a monomeric or polymeric crosslinking agent with at least two curable functional groups.

In a fourth aspect of the invention, there is provided a lubricious coating for coating a substrate surface in need thereof, comprising:

an adhesion promoting coating layer as described in the second aspect of the invention and any technically sensible combination of its embodiments as an adhesion promoting coating; and a lubricious coating layer comprising a second crosslinked polymer matrix formed by:

(a) curing at least one hydrophilic curable polymer having at least two curable functional groups with itself; or (b) curing of at least one hydrophilic curable polymer having at least one curable functional group in combination with a monomeric or polymeric crosslinking agent having at least two curable functional groups, where the monomeric or polymeric crosslinking agent has a molecular weight of from 200 to 5000 Daltons (e.g. from 200 to 1000, such as from 200 to 750 Daltons, from 300 to 600 Daltons).

In embodiments of the third and fourth aspects of the invention:
- (i) the functional group(s) on the at least one hydrophilic curable polymer having at least one or two curable functional groups may be selected from one or more of the group consisting of acrylate and methacrylate;
- (ii) the at least one hydrophilic curable polymer having at least one or two curable functional groups may be selected from one or more of the group consisting of hyaluronic acid, alginates, gelatin, chitin, or more particularly, polyethers, polyvinylpyrrolidone (PVP), polyesters, polyvinyl alcohols, polysaccharides and copolymers thereof, optionally wherein the at least one hydrophilic curable polymer having at least one or two curable functional groups may be selected from one or more of the group consisting of poly(ethylene glycol) (PEG), poly(propylene glycol) (PPG), PEG-co-PPG, PEG-co-PPG-co-PEG, poly(ε-caprolactone), polylactide, poly(lactide-co-glycolide), poly(ε-caprolactone-b-ethylene glycol-b-ε-caprolactone), poly(lactide-b-ethyleneglycol-b-lactide), poly[(lactide-co-glycolide)-b-ethylene glycol-b-(lactide-co-glycolide)], polyvinylpyrrolidone (PVP), and PVP-co-PEG, optionally wherein the least one or two curable functional groups may be acrylate;
- (iii) the monomeric or polymeric crosslinking agent may be selected from the group consisting of dipentaerythritol hexaacrylate, polybutadiene diacrylate, 1,10-decanediol diacrylate, tricyclodecane dimethanol diacrylate, dipropyleneglycol diacrylate, neopentylglycol propoxylate diacrylate, ditrimethylol propanetetraacrylate, ethoxylated pentaerythritol tetraacrylate, ethoxylated trimethylol propanetriacrylate, ethoxylated isocyanuric acid triacrylate, tripropylene glycoldiacrylate, pentaerythritol triacrylate, 1,10-dodecanediol dimethacrylate, ethoxylated cyclohexanedimethanol di(meth)acrylate, 2-hydroxy 1-3-dimethacryloxy propane, ethoxylated bisphenol A di(meth)acrylate, bisphenol A epoxy acrylate, diethylene glycol dimethacrylate, ethyleneglycol dimethacrylate, tricyclodecane dimethanol dimethacrylate, triethyleneglycol dimethacrylate, PEG diacrylate or PEG methacrylate, optionally wherein the monomeric crosslinker does not contain an amide group;
- (iv) the at least one hydrophilic curable polymer having at least one or two curable functional groups may have a number average molecular weight of from 20,000 to 200,000 Daltons; and/or
- (v) the at least one hydrophilic curable polymer having at least one or two curable functional groups may be a non-ionic linear, branched or crosslinked hydrophilic polymer; and/or
- (vi) the initiator may be a photoinitiator or a thermal initiator; and/or
- (vii) the solvent may be water and/or an organic solvent, optionally wherein the organic solvent may be selected from one or more of the group consisting of alcohols (e.g. methanol, ethanol, n-propanol, isopropanol, n-butanol, sec-butanol, t-butanol).

In embodiments of the third aspect of the invention:
- (i) the at least one hydrophilic curable polymer having at least two curable functional groups may be present in an amount of from 1 wt % to 15 wt %, the initiator may be present in an amount of from 0.05 wt % to 1 wt %, and the solvent may be present in an amount of from 84 wt % to 99 wt %;
- (ii) the at least one hydrophilic curable polymer having at least one curable functional group may be present in an amount of from 1 wt % to 15 wt %, the monomeric crosslinking agent may be present in an amount of from 0.2 wt % to 5 wt %, the initiator may be present in an amount of from 0.05 wt % to 0.6 wt %, and the solvent is present in an amount of from 80 wt % to 99 wt %.

In embodiments of the fourth aspect of the invention:
- (a) the polymeric adhesion promoter and the first crosslinked polymeric matrix may be physically bound together (e.g. the polymeric adhesion promoter and the first crosslinked polymeric matrix are physically bound together form an interpenetrating network);
- (b) the adhesion promoting coating layer and the lubricious coating layer may be interconnected by crosslinking between the first and second crosslinked polymer matrices;
- (c) the combined coating thickness of the adhesion promoting coating layer and the lubricious coating layer in a dry state may be from 50 nm to 50 μm (e.g. from 0.5 μm to 20 μm);
- (d) the lubricious coating is on a substrate surface, where the surface may be made from one or more of the group consisting of a metal, or a polymer, optionally wherein the polymer may be one or more of poly(ethene-co-tetrafluoroethene), polytetrafluoroethylene, or more particularly polyurethane, polyvinyl chloride, latex, pebax, nylon, polypropylene, polyethylene, fluorinated ethylene propylene and silicone elastomers;
- (e) in the adhesion promoting coating layer, the adhesion promoter may be present in an amount of equal to or less than 80 wt % of the adhesion promoting coating layer (e.g. from 15 wt % to 65 wt %);
- (f) in the adhesion promoting coating layer, the first crosslinked polymeric matrix may be present in an amount of from 20 wt % to 85 wt % (e.g. from 25 wt % to 75 wt %, from 25 wt % to 70 wt %, such as from 35 wt % to 65 wt %);
- (g) in the lubricious coating layer, when the second crosslinked polymer matrix is formed by curing at least one hydrophilic curable polymer having at least one curable functional group in combination with a monomeric or polymeric crosslinking agent having at least two curable functional groups, the at least one hydrophilic curable polymer having at least one curable functional group is present in an amount of above 35 wt % (e.g. above 55 wt %, such as from 55 wt % to 99.6 wt %), the monomeric or polymeric crosslinking agent is present in an amount of 0.5 wt % to 70 wt % (e.g. from 3 wt % to 30 wt %).

In a fifth aspect of the invention, there is provided a process to coat the whole or part of an article with a lubricious coating, comprising the steps of:
- (a) providing an article with at least one surface to be coated;
- (b) coating the at least one surface with an adhesion promoting coating formulation as described in the first aspect of the invention (or any technically sensible combination of its embodiments) to form a base-coated article;
- (c) subjecting the base-coated article to curing to form a cured, base-coated article;
- (d) coating the cured, base-coated article with a lubricious coating formulation as described in the third aspect of the invention (or any technically sensible combination of its embodiments) to provide an uncured lubricious-coated article; and (e) subjecting the uncured lubricious-coated article to curing to form a lubricious-coated article.

In embodiments of the invention, the curing in steps (c) and (e) of the process are conducted using ultraviolet curing conditions. In yet further embodiments of the invention the curing step (c) is conducted for a period of time $t_1$ that allows for crosslinking to occur between the base coat later and the top coat layer in step (e), such that the resulting coating on the coated article is stable over twenty cycles in a lubricity test.

In a sixth aspect of the invention, there is provided an article comprising a surface coated in a lubricious coating as described in the fourth aspect of the invention (or any technically sensible combination of its embodiments).

DRAWINGS

The invention may be described with reference to the accompanying figures.

FIG. 1 provides pictures of a PEBAX sample before (a) and after (b) coating.

DESCRIPTION

Figure 1:
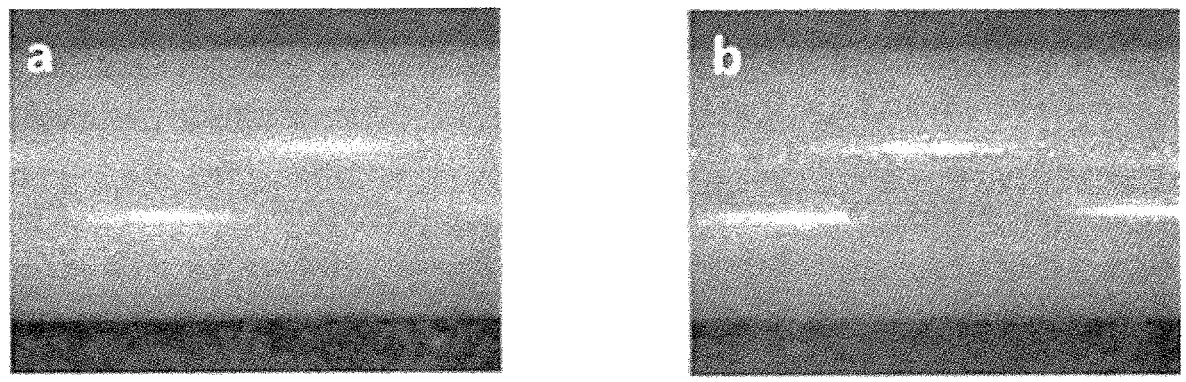

The lubricious coating of the current invention may comprise a base coating layer (adhesion promoting coating layer) and a top coating layer (lubricious coating layer). The base coating is formed by curing an adhesion promoting coating formulation that comprises a polymer/monomer with curable functional groups, an initiator, an adhesion promoter and a solvent. In the base coating layer (adhesion promoting coating layer), the curable polymer and the adhesion promoter are physically bound to each other or entrapped to form a polymer network after curing. The base coating layer (adhesion promoting coating layer) may also form covalent bonds with the top coating layer (lubricious coating layer) to develop a stable coating network.

While the functional or lubricious coating layer provides lubricity, the adhesion promoting coating layer offers stability to the composite coating. By tuning the hydrophobic substitution of the hydrophilic polymer in the adhesion promoting coating layer, it was found that it was possible to ensure good attachment of the adhesion promoting coating layer to a broad range of medical device substrates, such as metals, polyurethane (PU), polyvinyl chloride (PVC), latex, pebax, nylon, polypropylene, polyethylene (HDPE and LDPE), fluorinated ethylene propylene (FEP), poly(ethene-co-tetrafluoroethene) (ETFE), poly(ethylene terephthalate) (PET) and silicone elastomers etc. Some of these materials are very hydrophobic (low surface energy), such as PP, HDPE, FEP and ETFE, so it is difficult for a hydrophilic coating solution to spread on these surfaces spontaneously. Without wishing to be bound by theory, it is believed that this issue arises because these hydrophobic substrate surfaces have a much lower surface energy relative to the surface energy of the solvent used as part of the coating formulation for said substrate surface. This makes it difficult to effectively wet the substrate surface. As such, as a hydrophilic coating solution has a higher surface energy than that of the substrate, there is always a need to modify the substrate in some way to increase the surface energy of the substrate surface. The commonest way to achieve good adhesion in this circumstance is by using pre-treatment, such as oxidation of the surface or plasma treatment to generate polar groups on the substrate surface. However, such pre-treatment increases the manufacturing cost and lowers the efficiency of manufacturing. The current invention obviates this issue.

A lubricious coating layer can be formed by curing a hydrophilic curable polymer, an initiator, and a solvent with/without a hydrophilic crosslinking agent. An advantage of using a curable hydrophilic polymer with a crosslinker or a curable polymer that can crosslink with itself so that the entire polymer network is stable (due to crosslinking between all polymeric components) and results in minimal particles that can drop off and migrate when the device is deployed into a lumen of the human body. In contrast, when a fully-formed hydrophilic polymer that has no crosslinking ability is used in combination with a crosslinking agent that is cured to form a separate polymer, the level of migratable particles is much higher. It is believed that this is because the hydrophilic polymer is only entrapped in the supporting polymer network of the crosslinking agent (i.e. an interpenetrating network) and this means that the polymeric network is less stable, resulting in a higher level of migratable particles. In other words, when the hydrophilic polymer is only entrapped into a supporting network made from the crosslinked monomer material, the migratables will significantly increase in proportion to the increase of distance between two nodes in the supporting network, which is in turn related to the molecular weight of the monomer and its curing efficacy.

Advantages associated with the current invention are listed below.

(1) The coating formulations described herein are directly applicable to a wide variety of materials that are used in medical device manufacturing, including metals, polyurethane, polyvinyl chloride, latex, Pebax, nylon, polypropylene, polyethylene, fluorinated ethylene propylene, and silicone elastomers etc. Plasma or other chemical pre-treatment steps are not required to achieve a stable and homogeneous coating.

(2) The coating can achieve equal to or greater than 95% reduction of friction force for medical devices and maintain low particulate release even after multiple insertion/removal cycles.

(3) The coating has very low particulates/migratable release when applied on medical devices.

(4) Without wishing to be bound by theory, it is believed that the excellent stability and durability of certain lubricious coating described herein may be due to (a) the entangling or covalent bonding of the polymer networks in the base coating and top coating layers; and (b) strong adhesion between base coating polymer and the substrate.

(5) The coatings described herein can effectively trap water molecules inside the polymer network, which leads to a dry-out time that is more than 10 minutes.

(6) The lubricious coating technology described herein is based on UV curing, which enables a fully-formed homogeneous coating to be obtained in less than 5 minutes from the raw, uncoated article. Further, the processes described herein have a higher coating efficiency as compared with traditional heat curing, which requires several hours or more to obtain a coated product.

(7) Again, without wishing to be bound by theory, it is believed that the application of an adhesion promoter in the base coating makes the coating stable on a wide variety of materials.

(8) The coating is biocompatible.

Thus, there is provided a lubricious coating for coating a surface in need thereof, comprising:
an adhesion promoting coating layer comprising:
a polymeric adhesion promoter;
a first crosslinked polymeric matrix formed by a first monomeric or polymeric crosslinking agent, wherein the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group; and
a lubricious coating layer comprising a second crosslinked polymer matrix formed by:
(a) curing at least one hydrophilic curable polymer having at least two curable functional groups with itself; or
(b) curing of at least one hydrophilic curable polymer having at least one curable functional group in combination with a monomeric or polymeric crosslinking agent having at least two curable functional groups.

After wetting the coated article with water, the coating layer shows a very low friction force and a satisfactory adherence to the surface of the substrate used (e.g. as described in more detail below with reference to FIG. 3).

It will be appreciated that the term "at least one" when used herein may relate to one or more than one (e.g. 1, 2, 3, 4, 5, 6, 7, 8, 9 or 10, such as 1, 2 or 3) of the item to which said term is prefixed to. For example, when used in the phrase "curing at least one hydrophilic curable polymer . . . ", it will be appreciated that one or more (e.g. 1, 2, 3, 4, 5, 6, 7, 8, 9 or 10, such as 1, 2 or 3) hydrophilic curable polymers may be included in the adhesion promoting coating layer. Similarly, it will be appreciated that the term "at least two" when used herein may relate to two or more than two (e.g. 2, 3, 4, 5, 6, 7, 8, 9 or 10, such as 2 or 3) of the item to which said term is prefixed to. For example, when used in the phrase "at least two curable functional groups", it will be appreciated that two or more (e.g. 2, 3, 4, 5, 6, 7, 8, 9 or 10, such as 2, 3, 4, 5, 6 or 7) cross-linkable functional groups are present in each hydrophilic curable polymer chain included in the adhesion promoting coating layer and that the cross-linkable functional groups on each polymer chain may be the same or different, provided that they have a compatible partner on another polymer chain.

Thus, when used herein, the term "curing at least one hydrophilic curable polymer having at least two curable functional groups with itself", may refer to: the use of a single hydrophilic curable polymer having two identical functional groups on each polymer chain; the use of a single hydrophilic curable polymer having two different functional groups on each polymer chain, provided that the functional groups can form a crosslink (e.g. the two different functional groups can be a carboxylic acid group and an amino group or a carboxylic acid group and a hydroxyl group); the use of two hydrophilic curable polymers each having two identical functional groups on each polymer chain (that is, the functional groups may be the same on both polymers, thereby allowing a polymer network to form between both polymers, or different on both polymers, thereby allowing two separate but interpenetrating polymer networks to form); the use of two hydrophilic curable polymers each having two non-identical functional groups on each polymer chain (where the non-identical functional groups can enable a single polymeric network to form via cross-linking or two separate, but interpenetrating, polymer networks to form); or any other technically sensible combination.

When used herein, the term "lubricious" describes a slippery surface after wetting. More fully, a coating layer on medical device surface is considered to be "lubricious" if the friction force is less than 10% of the original friction force, under a clamp force of 300 g and a pulling speed of 1 cm/s, when measured at a temperature of 25±2° C. The testing protocol to measure whether an object is lubricious is provided in the Examples.

When used herein, the term "adhesion promoter" relates to a polymer that improves the adhesion of polymer onto a material surface (e.g. a substrate surface).

When used herein, the terms "hydrophilic" and "hydrophobic" relate to the hydrophilic-lipophilic balance (HLB) value calculated according to the Davies' Method using formula (1). A polymer is considered hydrophilic if the HLB>10, and hydrophobic if the HLB<10.

$$HLB = 7 + \sum_{i=1}^{m} H_i - n \times 0.475 \qquad (1)$$

where:
m is the number of hydrophilic groups in the molecule;
$H_i$ is the value of the $i^{th}$ hydrophilic groups (e.g. based upon the tables provided by Davies); and
n is the number of lipophilic groups in the molecule.

As mentioned herein, the polymeric adhesion promoter may have a hydrophilic backbone polymer with an HLB of >10. The hydrophilic backbone may have hydrophobic substituted groups. In addition, the polymeric adhesion promoter may also be a block copolymer comprising hydrophobic and hydrophilic blocks (i.e. the hydrophobic blocks may have a HLB<10 and the hydrophilic blocks may have a HLB>10).

When used herein, the term "comprising" is intended to require all components mentioned to be present, but to allow further components to be added. It will be appreciated that the term "comprising" also covers the terms "consisting of" and "consisting essentially of" as subsets, which are limited to only the components mentioned or to only the component mentioned along with some impurities, respectively. For the avoidance of doubt, it is explicitly contemplated that every use of the word "comprising" may be replaced with "consisting of" and "consisting essentially of" and variants thereof.

In certain embodiments of the invention, the base (adhesion promoting) coating layer and the top (lubricious) coating layer of the lubricious coating may be interconnected by crosslinking between the first and second crosslinked polymer matrices. Evidence of this crosslinking may be obtained from the examples, where a long cure time for the base coating layer may result in a coating that is undesirable. While not wishing to be bound by theory, it is believed that a degree of crosslinking between the base and top coating layers may be at least partly responsible for the good effects obtained in these embodiments.

The lubricious coating may have a thickness in a dry state of from 50 nm to 50 µm (e.g. from 0.5 µm to 20 µm).

It will be appreciated that the lubricious coating is intended to be applied to a surface (e.g. of a medical device). The surface may be made from one or more of the group consisting of a metal, or, more particularly, polyurethane, polyvinyl chloride, latex, pebax, nylon, polypropylene, polyethylene, fluorinated ethylene propylene, and silicone elastomers. Metals that may be mentioned herein include iron, steel (e.g. stainless steel), platinum, gold, silver, copper, nickel, titanium and alloys thereof. Alloys that may be mentioned herein include nitinol.

The base (adhesion promoting) coating layer of the lubricious coating may be one in which the polymeric adhesion promoter is present in an amount of equal to or less than 80 wt % of the base coating layer (e.g. from 15 wt % to 65 wt %); and/or the first crosslinked polymeric matrix is present in an amount of from 20 wt % to 85 wt % (e.g. from 25 wt % to 75 wt %, such as from 35 wt % to 65 wt %).

The top (lubricious) coating layer of the lubricious coating may be one in which the hydrophilic polymer is present in an amount of above 35 wt % (e.g. above 55 wt %, such as from 55 wt % to 99.6 wt %); and/or the second crosslinked polymer matrix is present in an amount of 0.5 wt % to 70 wt % (e.g. from 3 wt % to 30 wt %).

The top (lubricious) coating layer and the base (adhesion promoting) coating layer are formed from respective top (lubricious) and base (adhesion promoting) coating formulations, wherein an article having a surface is coated with the base (adhesion promoting) coating layer formulation and then subjected to curing, before being coated with the top (lubricious) coating layer formulation and subsequent curing thereof to form an article with a surface coated with the top (lubricious) and bottom (adhesion promoting) coating layers.

Thus, there is provided an adhesion promoting coating formulation for use in preparing the adhesion promoting coating layer described hereinbefore, comprising:
  a polymeric adhesion promoter;
  a first monomeric or polymeric crosslinking agent;
  a photoinitiator; and
  a solvent, wherein
  the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group.

The base (adhesion promoting) coating is formed by curing a layer of the base coating (adhesion promoting) formulation on an article. Without wishing to be bound by theory, the first monomeric or polymeric crosslinking agent and the adhesion promoter may be physically bound to each other or entrapped to form a polymer network after curing. Such a network provides good adherence to various substrate materials, including metals, or more particularly, polyurethane, polyvinyl chloride, latex, pebax, nylon, polypropylene, polyethylene, fluorinated ethylene propylene, and silicone elastomers etc.

The hydrophilic and/or hydrophobic polymer of the base (adhesion promoting) coating formulation is as described hereinbefore. Examples of the hydrophilic polymer that may be mentioned herein include:

(a) a block copolymer having hydrophobic and hydrophilic polymer blocks where,
  the hydrophilic block may be chosen from one or more of the group selected from polysaccharide (such as chitosan), poly(vinyl alcohol) (PVA), polymethacrylic acid, poly (ethylene glycol) (PEG), polyacrylamide (PAM), poly(2-oxazoline), and polyethylenimine (PEI), and
  the hydrophobic block may be chosen from one or more of the group selected from polystyrene (PS), polybutadiene (PB), polyisoprene (PI), poly(methyl methacrylate) (PMMA), poly(methylacrylate) (PMA), poly(propylene oxide) (PPO), poly(hydroxyethylmethacrylate) (PHEMA), poly(vinyl ether) (PVE), poly(vinyl methyl ether) (PVME), poly(vinyl butyl ether) (PVBE), polyimide and poly(dimethylsiloxane) (PDMS), poly(N-isopropylacrylamide) (PNIPAM) (e.g. the hydrophilic block may be chosen from poly (ethylene glycol) (PEG) and the hydrophobic block may be chosen from poly(propylene oxide) (PPO));
(b) a hydrophilic polymer comprising hydrophilic functional groups, where from 10% to 100% of the hydrophilic functional groups are capped with a hydrophobic functional group where,
  the hydrophilic polymer comprising hydrophilic functional groups is one or more of the group selected from polyethylenimine (PEI), polyacrylamide (PAM), polysaccharide, and poly(vinyl alcohol) (PVA), and
  the hydrophobic functional group caps one or two hydrophilic functional groups and is selected from one or more of methylene ($CH_2$), methyl ($CH_3$), ethylene ($CHCH_3$), ethyl ($CH_2CH_3$), $C_{3-6}$ alkyl, and $C_{3-6}$ alkylene (e.g. $CH(CH_2)_2CH_3$), where the latter two groups are unsubstituted or substituted by a hydroxyl group.

When used herein, it will be understood that methylene, ethylene and $C_{3-6}$ alkylene, such as $CH(CH_2)_2CH_3$ refer to acetal functional groups where a carbon atom is bound to two oxygen atoms. For example, in methylene ($CH_2$), the single carbon atom is bound to two oxygen atoms to form an acetal, for ethylene ($CHCH_3$), the carbon atom attached to a single hydrogen atom is bound to two oxygen atoms and this is also the case for $CH(CH_2)_2CH_3$.

When used herein, unless otherwise stated, "poly(propylene oxide) (PPO)" and "polyethylene glycol (PPG)" may be used interchangeably.

For the avoidance of doubt, the polymers and blends of group (a) and (b) may be used alone or in combination with each other.

As noted above, the polymeric adhesion promoter may be a hydrophilic polymer comprising hydrophilic functional groups, where from 10% to 100% of the hydrophilic functional groups are capped with a hydrophobic functional group. It will be appreciated that "100%" refers to the total capping of all hydrophilic functional groups, whereas "10%" refers to the capping of 10% of the total number of hydrophilic functional groups. In certain embodiments, the capping of the hydrophilic functional groups may be from 25% to 100% (e.g. from 30% to 100%, such as from 35% to 100%, from 50% to 75% or from 30% to 50%). Suitable hydrophilic polymers with hydrophilic functional groups are mentioned hereinbefore. A suitable capped hydrophilic polymer comprising hydrophilic functional groups is poly(vinyl alcohol) (PVA), where an acetal functional group (e.g. $CH(CH_2)_2CH_3$) caps two hydroxyl groups pendant to the PVA polymer backbone.

In certain embodiments, the polymeric adhesion promoter of the base (adhesion promoting) coating formulation may:
  (a) have a number average molecular weight of 20,000 to 2,000,000; and/or
  (b) be linear, branched or crosslinked.

As described hereinbefore, the base (adhesion promoting) coating layer of the lubricious coating contains a first crosslinked polymeric matrix, this matrix being formed by use of a first monomeric or polymeric crosslinking agent. The first monomeric or polymeric crosslinking agent may be a monomer or polymer with at least two functional groups capable of crosslinking, optionally:

(a) each of the at least two functional groups are selected from acrylate and methacrylate; and/or
(b) when the first monomeric or polymeric crosslinking agent is a polymer, the polymer is a polyester or polyether (e.g. the polymer is a polyester or polyether that does not contain an amide functional group).

Examples of the first monomeric or polymeric crosslinking agent that may be mentioned herein include one or more selected from the group consisting of butanediol dimethacrylate, bisphenol diacrylate, tricyclodecane dimethanol diacrylate, pentaerythritol triacrylate, epoxy acrylate/methacrylate oligomer, polyester acrylate/methacrylate oligomer, and acrylic acrylate oligomer. Examples of suitable epoxy acrylate oligomers, polyester acrylate oligomers, and acrylic acrylate oligomers may be selected from the group consisting of bisphenol A epoxy acrylate, tripropylene glycol diacrylate, propoxylated neopentyl diacrylate, ethoxylated bisphenol A diacrylate, bisphenol A ethoxylate dimethacrylate, propoxylated glycerol diacrylate, ditrimethylolpropane tetraacrylate, dipentaerythritol pentaacrylate, dipentaerythritol penta/hexa-acrylate, tripropylene diacrylate, trimethylol propane ethoxylate triacrylate, trimethylol propane propoxylate triacrylate, di(trimethylolpropane) tetraacrylate, glycerol propoxylate triacrylate, pentaerythritol propoxylate triacrylate, poly(ethylene glycol) diacrylate, poly(propylene glycol) diacrylate, and tri(propylene glycol) diacrylate. It will be appreciated that mixtures or blends of acrylate/methacrylate polymers/monomers may be used in the practice of the invention. In certain embodiments, the first monomeric or polymeric crosslinking agent may have a molecular weight of from 200 to 50,000 Daltons (e.g. from 200 to 10,000 Daltons, from 400 to 5,000 Daltons, such as from 400 to 2,000 Daltons). Particular first monomeric or polymeric crosslinking agents that may be mentioned include a polyether with at least two curable acrylate and/or methacrylate groups (e.g. molecular weight of from 200 to 50,000 Daltons (e.g. from 200 to 10,000 Daltons, such as from 400 to 5,000 Daltons or from 400 to 2,000 Daltons)).

For the avoidance of doubt, molecular weight of any polymer or oligomer mentioned herein is based upon the number average molecular weight.

The base coating formulation as described hereinbefore may comprise the following amounts of the constituent components:

the polymeric adhesion promoter is present in an amount of from 0.05 wt % to 10 wt % (e.g. from 0.1 wt % to 5 wt %);
the first monomeric or polymeric crosslinking agent is present in an amount of from 0.2 wt % to 7 wt %;
the photoinitiator is present in an amount of from 0.01 wt % to 2 wt %; and
the solvent is present in an amount of from 92 wt % to 99 wt %, (e.g. the hydrophilic and/or hydrophobic polymer is present in an amount of from 0.1 wt % to 5 wt %, the first monomeric or polymeric crosslinking agent is present in an amount of from 0.6 wt % to 5 wt %, the photoinitiator is present in an amount of from 0.1 wt % to 1 wt %, and the solvent is present in an amount of from 94 wt % to 98 wt %).

It will be appreciated that the adhesion promoting coating formulation described herein before can be used to provide an adhesion promoting coating for forming a base coating layer on a substrate material onto which a lubricious top layer coating can be formed. Said adhesion promoting coating may comprise:

a polymeric adhesion promoter;
a first crosslinked polymeric matrix formed by a first monomeric or polymeric crosslinking agent, wherein
the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group. it will be appreciated that the constituent components are described hereinbefore with respect to the adhesion promoting coating formulation.

Thus, there is also provided a top (lubricious) coating formulation for use in preparing the top coating layer of the lubricious coating described hereinbefore, comprising:

a solvent;
an initiator; and
at least one hydrophilic curable polymer having at least two curable functional groups or at least one hydrophilic curable polymer with at least one curable functional group and a monomeric or polymeric crosslinking agent with at least two curable functional groups.

A hydrophilic polymer will swell when water is added to it (i.e. when it gets wet). This hydrophilic nature may be introduced by the use of ionic groups (e.g. acid or salt moieties) or non-ionic groups (e.g. ethoxy ethers or amide moieties). Hydrophilic polymer matrixes of the top (lubricious) coating layer that may be mentioned herein include two possibilities, both of which use a curable hydrophilic polymer with at least one or two curable functional groups. When the hydrophilic polymer has at least one curable functional group (e.g. only one curable functional group), the formulation may be supplemented with a curable polymeric or monomeric crosslinking agent. In certain embodiments that may be mentioned herein, the curable polymers mentioned herein may be a non-ionic hydrophilic polymer without amide moieties.

In the lubricious coating formulation described herein, the functional group(s) on the at least one hydrophilic curable polymer having at least one or two curable functional groups may be selected from one or more of the group consisting of acrylate and methacrylate.

The at least one hydrophilic curable polymer having at least one or two curable functional groups may be a non-ionic linear, branched or crosslinked hydrophilic polymer. Suitable hydrophilic polymers for use in the lubricious coating formulation that may be mentioned include hyaluronic acid, alginates, gelatin, chitin, or more particularly, polyethers, polyvinylpyrrolidone (PVP), polyesters, polyvinyl alcohols, polysaccharides, and copolymers thereof. For example the hydrophilic polymer for use in the lubricious coating formulation may be one or more of poly(ethylene glycol) (PEG), poly(propylene glycol) (PPG), PEG-co-PPG, PEG-co-PPG-co-PEG, poly(ε-caprolactone), polylactide, poly(lactide-co-glycolide), poly(ε-caprolactone-b-ethylene glycol-b-ε-caprolactone), poly(lactide-b-ethyleneglycol-b-lactide), poly[(lactide-co-glycolide)-b-ethylene glycol-b-(lactide-co-glycolide)], polyvinylpyrrolidone (PVP), and PVP-co-PEG, optionally wherein the at least one or two curable functional groups may be acrylate.

Molecular weights for the at least one hydrophilic curable polymer having at least one or two curable functional groups that may be mentioned herein range from a number average molecular weight of 20,000 Daltons to a number average molecular weight of 200,000 Daltons.

Suitable monomeric or polymeric crosslinking agents used in the lubricious coating formulation that may be mentioned herein include dipentaerythritol hexaacrylate, polybutadiene diacrylate, 1,10-decanediol diacrylate, tricyclodecane dimethanol diacrylate, dipropyleneglycol diacrylate, neopentylglycol propoxylate diacrylate, ditrimethylol propanetetraacrylate, ethoxylated pentaerythritol tetraacrylate, ethoxylated trimethylol propanetriacrylate, ethoxylated isocyanuric acid triacrylate, tripropylene glycoldiacrylate, pentaerythritol triacrylate, 1,10-dodecanediol dimethacrylate, ethoxylated cyclohexanedimethanol di(meth)acrylate, 2-hydroxy 1-3-dimethacryloxy propane, ethoxylated bisphenol A di(meth)acrylate, bisphenol A epoxy acrylate, diethylene glycol dimethacrylate, ethyleneglycol dimethacrylate, tricyclodecane dimethanol dimethacrylate, triethyleneglycol dimethacrylate, PEG diacrylate or PEG methacrylate, optionally wherein the monomeric crosslinker does not contain an amide group. The monomeric or polymeric crosslinking agent has a molecular weight of from 200 to 5000 Daltons (e.g. from 200 to 1000 Daltons, such as from 200 to 750 Daltons, such as from 300 to 600 Daltons).

The base coating formulation and the top coating formulation also include an initiator. The initiator is present to initiate the polymeric chain reaction of monomeric or polymeric crosslinking agents when the top and base coating formulations are subject to curing, as described in more detail below. Typical initiators that may be used in the current invention include thermal initiators and photoinitiators and mixtures thereof. In particular embodiments of the invention, the initiator used in the adhesion promoting coating formulation and/or the lubricious coating formulation may be a photoinitiator (e.g. a Norrish type I photoinitiator, amongst other possible options).

General classes of photoinitiators that may be mentioned herein include α-hydroxyketones, phenylglyoxylate, α-aminoketones, mono acyl phosphine, bis acryl phosphine and mixtures thereof. Examples of photoinitiators that may be used include one or more of benzophenone, benzyldimethyl ketal, isopropylthioxanthone, bis(2,6-dimethoxybenzoyl)(2,4,4-trimethylpentyl) phosphineoxide, 2-hydroxy-2-methyl-1-phenyl-1-propanone, diphenyl(2,4,6-trimethylbenzoyl) phosphine oxides, 1-hydroxycyclohexyl phenyl ketone, 2-benzyl-2-(dimethylamino)-1-4-(4-morpholinyl)phenyl-1-butanone, α,α-dimethoxy-α-phenylaceto-phenone, 2,2-diethoxyacetophenone, 2-methyl-1-4-(methylthio)phenyl-2-(4-morpholinyl)-1-propanone, 2-hydroxy-1-4-(2-hydroxyethoxy)phenyl-2-methyl-1-propanone, 1-hydroxycyclohexyl-phenyl-ketone, methylbenzoylformate, oxyphenyl-acetic acid 2-[2-oxo-2-phenyl-acetoxy-ethoxy]-ethyl ester, oxy-phenol-acetic 2-[2-hydroxy-ethoxy]-ethyl ester, 2-benzyl-2-(dimethylamino)-1-[4-(4-morpholinyl) phenyl]-1-butanone and 2-methyll-1-[4-(methylthio)phenyl]-2-(4-morpholinyl)-1-propanone.

Thermal initiators that may be mentioned herein include one or more selected from the group consisting of 4,4-azobis (4-cyanovaleric acid), 2,2'-azobisisobutyronitrile, lauroyl peroxide, benzoyl peroxide, dicumyl peroxide, decanoyl peroxide, di(n-propyl)peroxydicarbonate, 1,1-bis(tert-butylperoxy)cyclohexane, di(sec-butyl)peroxydicarbonate, t-butyl peroxyneodecanoate, di-t-butyl peroxide, di-t-amyl peroxide, (t-butylperoxy)butyrate, t-butyl peroxybenzoate, and di-t-butyl peroxyoxalate, 2,2-bis(tert-butylperoxy)butane, and potassium persulfate.

As is stipulated above, the base coating formulation and the top coating formulation described herein requires the presence of a solvent. The solvent may be water and/or an organic solvent. Organic solvents that may be mentioned herein include one or more selected from the group consisting of alcohols (e.g. methanol, ethanol, n-propanol, isopropanol, n-butanol, sec-butanol, t-butanol). Particular solvents that may be mentioned herein include methanol, ethanol, n-propanol, isopropanol, n-butanol, sec-butanol, and t-butanol.

When the lubricious coating formulation relates to at least one hydrophilic curable polymer having at least two curable functional groups, the at least one hydrophilic curable polymer having at least two curable functional groups may be present in an amount of from 1 wt % to 15 wt %, the initiator may be present in an amount of from 0.05 wt % to 1 wt %, and the solvent may be present in an amount of from 84 wt % to 99 wt %. When the lubricious coating formulation relates to at least one hydrophilic curable polymer having at least one curable functional group, the at least one hydrophilic curable polymer having at least one curable functional group may be present in an amount of from 1 wt % to 15 wt %, the monomeric crosslinking agent may be present in an amount of from 0.2 wt % to 5 wt %, the initiator may be present in an amount of from 0.05 wt % to 0.6 wt %, and the solvent may be present in an amount of from 80 wt % to 99 wt %. It will be appreciated that the lubricious coating layer will not contain the solvent when it has been formed (or only a minor remnant thereof in its dry state) and so to the proportions of the remaining components are increased proportionately.

In order to prepare the lubricious coating described herein before, it will be appreciated that both the adhesion promoting coating formulation and lubricious coating formulation are required. Thus, it is contemplated that both formulations will be provided as a kit of parts, that is as a kit of parts for forming a lubricious coating on a substrate surface in need thereof, said coating comprising an adhesion promoting coating layer directly on the surface of the substrate and a lubricious coating layer on the adhesion promoting coating layer, the kit comprising:
  (a) an adhesion promoting coating formulation as described hereinbefore; and
  (b) a lubricious coating formulation as described hereinbefore.

The lubricious coating as described herein contains both an adhesion promoting coating layer (i.e. in direct contact with the surface of a substrate) and a lubricious coating layer. In said lubricous coating:
  (a) the polymeric adhesion promoter and the first crosslinked polymeric matrix may be physically bound together (e.g. the polymeric adhesion promoter and the first crosslinked polymeric matrix may be physically bound together form an interpenetrating network); and/or
  (b) the adhesion promoting coating layer and the lubricious coating layer may be interconnected by crosslinking between the first and second crosslinked polymer matrices; and/or
  (c) the combined coating thickness of the adhesion promoting coating layer and the lubricious coating layer in a dry state may be from 50 nm to 50 μm (e.g. from 0.5 μm to 20 μm); and/or
  (d) the lubricious coating is on a substrate surface, where the surface may be made from one or more of the group consisting of a metal, or a polymer, optionally wherein the polymer is one or more of polyurethane, polyvinyl chloride, latex, pebax, nylon, polypropylene, polyethylene, fluorinated ethylene propylene, poly(ethene-co-tetrafluoroethene), polytetrafluoroethylene and silicone elastomers; and/or (e) in the adhesion promoting coating layer (e.g. in the dry state), the adhesion promoter may be present in an amount of equal to or less than 80 wt % of the adhesion promoting coating layer (e.g. from 15 wt % to 65 wt %); and/or (f) in the adhesion promoting coating layer (e.g. in the dry state), the first crosslinked polymeric matrix is present in an amount of from 20 wt % to 85 wt % (e.g. from 25 wt % to 75 wt %, such as from 25 wt % to 70 wt %, such as from 35 wt % to 65 wt %); and/or (g) in the lubricious coating layer, when the second crosslinked polymer matrix is formed by curing at least one hydrophilic curable polymer having at least one curable functional group in combination with a monomeric or polymeric crosslinking agent having at least two curable functional groups, the at least one hydrophilic curable polymer having at least one curable functional group may be present in an amount of above 35 wt % (e.g. above 55 wt %, such as from 55 wt % to 99.6 wt %), the monomeric or polymeric crosslinking agent is present in an amount of 0.5 wt % to 70 wt % (e.g. from 3 wt % to 30 wt %).

As discussed above, the base (adhesion promoting) coating formulation and the top (lubricious) coating formulation may be used in a process to coat an article. Thus, there is further disclosed a process to make an article coated in a lubricious coating as described hereinbefore, comprising the steps of:

(a) providing an article with at least one surface to be coated;
(b) coating the at least one surface with a base (adhesion promoting) coating formulation as described hereinbefore to provide a base-coated article;
(c) subjecting the base-coated article to curing to form a cured, base-coated article;
(d) coating the cured, base-coated article with a top (lubricious) coating formulation as described hereinbefore to provide an uncured lubricious-coated article; and
(e) subjecting the uncured lubricious-coated article to curing to form a lubricious-coated article.

The coating solutions can be cured using any suitable means, such as by UV light, visible light, and heat. In particular embodiments of the invention, the curing in steps (c) and (e) may be conducted using ultraviolet curing conditions.

In certain embodiments of the invention, in the process described above curing step (c) may be conducted for a period of time $t_1$ that allows for crosslinking to occur between the base coat later and the top coat layer in step (e), such that the resulting coating on the coated article is stable over twenty cycles in a lubricity test.

Without wishing to be bound by theory, it is speculated that ensuring that a substantial proportion of the crosslinking groups in the first crosslinked polymeric matrix remain free enables covalent bonds to be formed by crosslinking between the base coating layer and the top coating layer when the top coating layer is subjected to curing conditions in step (e) of the process above.

As will be appreciated the process provides an article, which article contains the lubricious coating as described hereinbefore.

Further aspects of the invention will now be described with reference to the examples, which are not intended to limit the spirit and scope of the invention and/or the variants that are encompassed by the scope of the claims.

EXAMPLES

Materials and Methods

Synthesis of Copolymer PVP-PEG-AA with Acrylate Functional Groups

Copolymer PVP-PEG was prepared by radical copolymerization in water using a redox system ammonium persulfate and N,N,N',N',-tetramethylethylenediamine as an initiator. 1-Vinyl-2-pyrrollidone (NVP, Aldrich, 99%) 10 g and Poly(ethylene glycol) methacrylate (PEGMA, Mn 500) (Aldrich, 99%) 2.25 g were dissolved in 50 mL water under a nitrogen atmosphere. Ammonium persulfate (0.02 g) and N,N,N',N'-tetramethylethylenediamine (0.02 g) in water were added dropwise to the above. The mixture was allowed to react at 45° C. for 8 h. The unreacted monomers were removed by using the dialysis method. The resulting PVP-PEG copolymer was freeze-dried and was then re-dissolved at 45° C. in dry chloroform (Merck). Triethylamine (Aldrich) was added to the chloroform solution, followed by the drop wise addition over 1 h of acryloyl chloride (Aldrich) dissolved in 50 mL of dry chloroform. The reaction mixture was stirred for 8-12 hours at 45° C. under a nitrogen atmosphere. The solvent was then removed under reduced pressure. After concentration of the solution the resulting copolymer PVP-PEG with acrylate (PVP-PEG-AA) functional groups was then precipitated using diethyl ether.

Base (Adhesion Promoting) Coating Solutions

Base coating solutions were prepared by mixing the components together in the amounts indicated below in Table 1.

TABLE 1

| Ingredients | Formula No. (wt %) | | | | | | |
| --- | --- | --- | --- | --- | --- | --- | --- |
| | 1-1 | 1-2 | 1-3 | 1-4 | 1-5 | 1-6 | 1-7 |
| Trimethlolpropaneethoxylate-triacrylate | 1 | 0.6 | 1.8 | 2.8 | 3.1 | 1.8 | 1.8 |
| Poly(ethylene oxide) (MW 1,300,000) | 0.35 | 0.19 | — | — | — | — | |
| Poly(ethylene glycol)-Poly(propylene glycol) co-polymer | — | — | — | 2.1 | 2.0 | 1.2 | |
| Poly(ethylene oxide) (MW 100,000) | — | — | — | — | — | 0.5 | |

TABLE 1-continued

| Ingredients | Formula No. (wt %) | | | | | | |
|---|---|---|---|---|---|---|---|
| | 1-1 | 1-2 | 1-3 | 1-4 | 1-5 | 1-6 | 1-7 |
| Poly(vinyl butyral) (25% conversion of hydroxyl groups from poly(vinyl alcohol)) (Mw 130,000) | | | 2.0 | | | | |
| Poly(vinyl butyral) (75% conversion of hydroxyl groups from poly(vinyl alcohol)) (Mw 130,000) | | | | | | | 2.4 |
| 2-hydroxy-2-methyl-1-phenyl-1-propanone | 0.2 | 0.05 | 0.25 | 0.2 | 0.2 | 0.25 | 0.25 |
| Isopropanol | 98.45 | 97.83 | 94.25 | 94.9 | 93.6 | 93.75 | 95.55 |
| Water | 0 | 1.33 | 1.7 | 0 | 1.1 | 2.5 | 0 |
| Total % | 100 | 100 | 100 | 100 | 100 | 100 | 100 |

Top (Lubricious) Coating Solutions

Top coating solutions were prepared by mixing the components together in the amounts indicated below in Table 2.

TABLE 2

| | 2-1 | 2-2 | 2-3 | 2-4 |
|---|---|---|---|---|
| Bisphenol A dimethacrylate (MW 364) | 2 | — | — | — |
| Poly(ethylene glycol) diacrylate (MW 575) | — | — | 2 | — |
| Poly(ethylene glycol) diacrylate (MW 5000) | | | | 2 |
| PVP-PEG (with acrylate functional groups) | — | 13.8 | 8.7 | 8.7 |
| PVP (MW 1,300,000) | 5 | — | — | — |
| 2-hydroxy-1-4-(2-hydroxyethoxy)phenyl-2-methyl-1-propanone | 0.1 | 0.1 | 0.1 | 0.1 |
| Isopropanol | 82.9 | 61.1 | 64.2 | 64.2 |
| Water | 10 | 25 | 25 | 25 |
| Total % | 100 | 100 | 100 | 100 |

General Procedure 1

Coating and Curing Process

A catheter sample was first dip-coated with a base (or adhesion promoting) coating solution as described above at a dipping and pulling speed of 1 cm/s. The sample dipped in the base coat was then cured under an UV lamp with an UV density of 25-45 mW/cm² for at least 15 seconds. The cured, base-coated sample was then dip-coated with a top (or lubricious) coating solution using the same dipping and withdrawing speed and then subjected to UV curing (at the same UV density) for at least 30 seconds.

Morphology Observation

Each cured sample was examined under a microscope (10×; Zoom stereo microscope TXB2-D 10 with digital eye piece YYEYE01-130 & ring light HX6060LED-2, Nanyang city state optical instrument manufactory).

Lubricity Test

The lubricity of the samples was characterized according to ASTM D1894-Standard Test Method for Static and Kinetic Coefficients of Friction of Plastic Film and Sheeting.

Testing temperature: 25±3° C.

Clamp force: 300 g

Pulling speed: 1 cm/s

The measured friction obtained from the test was imputed into the equation below to obtain the coefficient of friction.

$$\text{Coefficient of Friction } (COF) = \frac{\text{Measured Friction (g)}}{\text{Clamp Force (g)}}$$

The lubricity test was repeated a set number of times (e.g. 20 times) and the COF was calculated following each cycle using the measured friction.

Stability Test

The coating was considered as stable if the sample remained lubricious following 20 cycles of lubricity testing (as described above). If there was a significant variation in the measured friction, the coating was considered as unstable as an increase in the measured friction value during the lubricity test may result from the peeling of the coating from the surface of the sample.

Particulate Test

The particulate test was performed on coated samples according to USP 788—Particulate Matter in Injections. The guide catheter was hydrated with about 10 mL of particle-free water. The coated Percutaneous transluminal coronary angioplasty (PTCA) catheter sample was inserted through guide catheter through a guidewire, which is to simulate the use with device. The PTCA catheter was retracted a clinically significant number of times. After retraction, the guide catheter and in-vitro model was flushed with about 40 mL of particle-free water. The effluent was collected and measured by a Liquid Particle Counter.

EXAMPLES

Example 1—Effect of the Base and Top Coat on Coating Performance of Pebax™ Tubing Eight catheter samples made of PEBAX™ tubing were subjected to dip coated according to General procedure 1, except for sample 8, where the PEBAX™ tubing was directly coated with the top-coating solution in accordance with the top-coating method outlined in General Procedure 1. The various base and top coating solutions are outlined in Table 3, as are results of the tests conducted to establish lubricity and stability conducted in accordance with the lubricity and stability measurement procedures described hereinbefore.

longer UV curing time of 120 seconds (instead of 15 seconds) for its base coating. The appearance of the samples were examined before and after wetting in water, and tested

TABLE 3

| Sample No. | Base Coating solution used (in formula no.) | Top Coating solution used (in fomula no.) | Appearance before wetting in water | Lubricity before coating (COF-1) | Lubricity after coating (COF-2) | Stability |
|---|---|---|---|---|---|---|
| 1 | 1-1 | 2-3 | Some rough patches on the surface | 1.03 | — | Coating was peeled off after 5th cycle |
| 2 | 1-2 | 2-3 | Some rough patches on the surface | 1.05 | — | Coating was peeled off after 9th cycle |
| 3 | 1-3 | 2-3 | Homogenous and glossy | 1.08 | 0.033 | Stable |
| 4 | 1-4 | 2-3 | Homogenous and glossy | 1.09 | 0.032 | Stable |
| 5 | 1-4 | 2-4 | Homogenous and glossy | 1.11 | 0.032 | Stable |
| 6 | 1-4 | 2-2 | Homogenous and glossy | 1.05 | 0.031 | Stable |
| 7 | 1-4 | 2-1 | Homogenous and glossy | 1.06 | 0.025 | Stable |
| 8 | — | 2-1 | Solution does not wet the surface. Non-homogeous | 1.06 | — | — |

The testing results for sample 8 shows that use of a top coating alone is not sufficient to wet the surface of PEBAX™ catheter. In contrast, samples 1-7 shows that coating the catheter using a combination of a base coat and a top coat improves the surface wetting ability of the hydrophilic top coating on a PEBAX™ catheter.

Table 3 allows a comparison of the stability between samples 1 to 4, which indicates that the base coating determines the adhesion of the whole coating layer onto the surface of the substrate material. In other words, it appears that a homopolymer of PEO is less suited for use as an adhesion promoter in a base coat applied to PEBAX™ than Poly(ethylene glycol)-Poly(propylene glycol) co-polymer and Poly(vinyl butyral) (25% conversion of hydroxyl groups from poly(vinyl alcohol) (Mw 130,000).

The COF values for samples 4 and 7 after coating shows that all three types of top coating exhibit sufficient lubricity and stability. Sample 8 does not include a curable polymer in the top coating layer and this results in a gradual decrease in the lubricity of the coating following each friction test, possibly due to the gradual release of the hydrophilic polymer from the top coating layer surface. In contrast, sample 4 to 7 retain a stable and lubricious top coating throughout the 25 test cycles, suggesting that the crosslinked network formed in at least the top coating layer eliminates the effect of coating abrasion from the surface of the coated device (e.g. during application of the catheter) that occurs when a hydrophilic hydrogel is used alone as the top coating.

Figure 2:
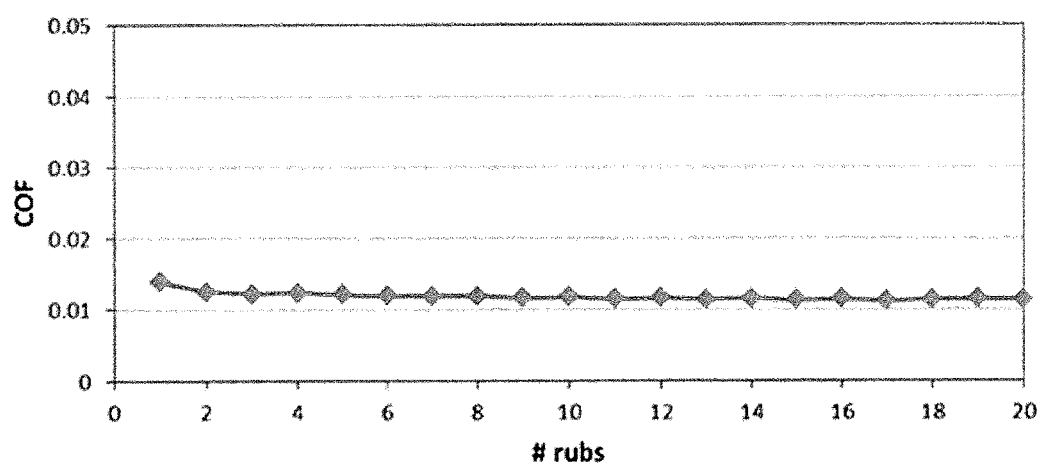
FIG. 2 depicts the coefficient of friction for sample 9 during 20 cycles of friction tests.

Example 2—Effect of UV Curing Duration for Base Coating on Overall Coating Performance Base coating formula 1-4 and top coating formula 2-3 were chosen for further studies. These coatings were applied to two catheter samples of PEBAX™ tubing using General Procedure 1, except that one sample was subjected to a for lubricity and stability. The results are presented in Table 4. The morphology and friction test curve are shown in FIGS. 1 and 2, respectively.

TABLE 4

| Sample Number | 9 | 10 |
|---|---|---|
| Base Coating UV curing time (seconds) | 15 | 120 |
| Top Coating UV curing time (seconds) | 60 | 200 |
| Appearance before wetting in water | Homogeneous and glossy | Homogeneous and glossy |
| Appearance after wetting in water | Homogeneous and smooth | Surface smooth, but less lubricious |
| Lubricity before coating/COF_1 | 1.12 | 1.09 |
| Lubricity after coating/COF_2 | 0.012 | 0.26 |
| Stability | Stable | A few points falling off |

The test results of sample 10 shows that increasing the curing time of the base coating results in a less lubricious and stable coating layer after wetting and friction test. This suggests that the base coating may be covalently bonded with the top coating through acrylate crosslinking, resulting in an interpenetrating cross-linked network between the base coating and the top coating. The presence of such inter-layer crosslinks appears to enhance the stability of the coating. In other words, and without wishing to be bound by theory, it appears that increasing the curing time of the bottom coating layer may result in fewer available "free" crosslinking sites on the bottom layer, resulting in fewer inter-layer crosslinks being formed, which in turn results in a less homogeneous and less stable top-layer.

Example 3—Effect of Hydrophobic Substitution on Hydrophilic Backbone of Adhesion Promoter The hydrophobic substitution of the hydrophilic backbone of adhesion promoter was studied. In this example, PVA was used as the hydrophilic backbone polymer and was modified by using butyraldehyde, so as to form acetals. By tuning the % of substitution of the hydroxyl group on PVA, different adhesion properties in the base coating can be achieved.

The top coating used in this example is 2-3, with the base coating formulation being based upon 1-3 (2.0 wt % of the polymer), though with a variable amount of hydrophobic group. These formulations were applied to different substrates made of latex, silicone and Pebax™ The maximum number of friction test repetitions was set at 90.

Figure 3:
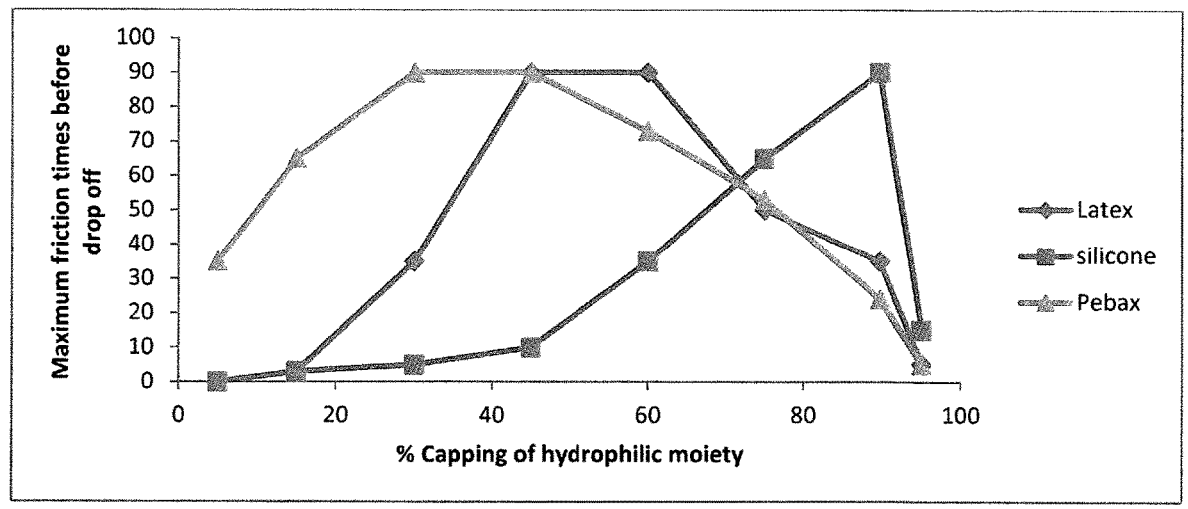
FIG. 3 depicts the relationship between the hydrophobic substitution on adhesion promoter and the number of friction tests that the resulting coating can sustain before drop off.

As shown in FIG. 3, the optimal level of capped hydroxyl groups by butyraldehyde differs depending on the substrate material in question. If the hydrophobicity of the hydrophilic polymer increases to a very high level, it may also create a wetting problem for the hydrophilic top coating layer. Therefore, there is an optimal value for the substitution percentage. In general, when a sample can survive the friction test more than 50 times the coating is stable for the desired application. FIG. 3 further shows that PVA with 45-75% capping of the hydrophilic moiety can provide good adhesion for both latex and Pebax™ However, because the silicone surface substrate is very hydrophobic, a 75-90% capping of the hydrophilic moiety is needed to achieve good adhesion and the desired stability. This shows that the current preparations can be tailored to suit the surface properties of the desired substrate.

Example 4—Effect of Hydrophobic/Hydrophilic Molar Ratio of Copolymer as Adhesion Promoter The hydrophobic/hydrophilic molar ratio of the copolymer of the adhesion promoter was studied. In this example, PEG-PPG copolymer was used. By tuning the number of PG polymer blocks and EG polymer blocks (ethylene glycol blocks), different adhesion properties in the base coating can be achieved.

Figure 4:
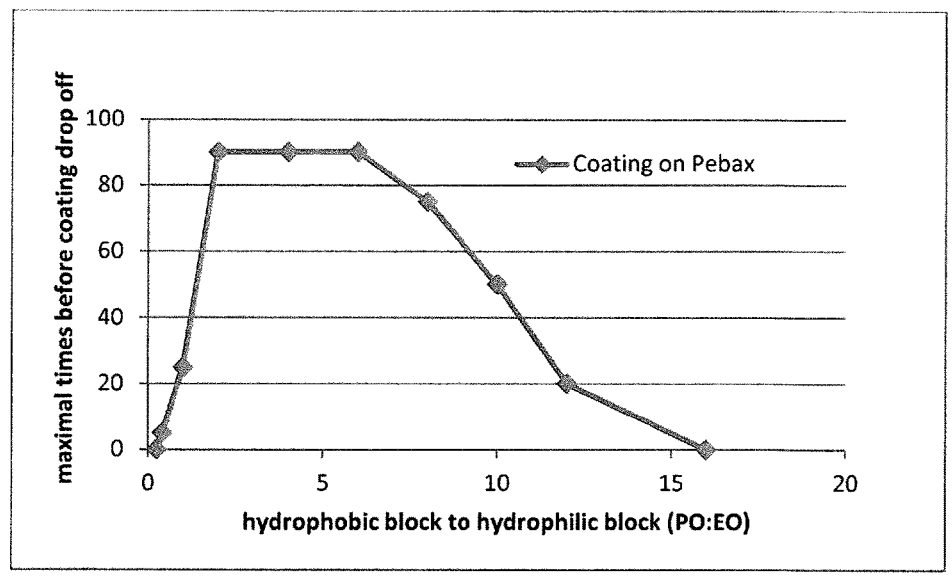
FIG. 4 depicts the relationship between the ratio PO unit/EO unit and the number of friction times that a coating can sustain before drop off.

The top coating used in this example is 2-3, with the base coating formulation being based upon 1-4, though with a variable amount of PG and EG blocks. The coating on Pebax is mechanically stable when the ratio of PG blocks/EG blocks is in the range of 2 to 6, as shown in FIG. 4. The coating tends to fall off if the hydrophobicity of the copolymer is too high due to increasing PG monomer unit content.

Example 5—Effect of Dry-Out Time on Coating Performance of a Latex Catheter

An important property of a urinary catheter is the dry-out time. The dry-out time determines the time a patient can wait before inserting the catheter and/or before withdrawing the catheter. A coating is not considered to be lubricious if the COF is above 10% of the COF before coating.

Catheter samples made of latex were coated as shown in Table 5 using General Procedure 1. The samples were examined and tested for lubricity and stability and the results are also presented in Table 5.

TABLE 5

| Sample No. | 11 | 12 | 13 |
| --- | --- | --- | --- |
| Base coat (in formula no.) | 1-6 | 1-6 | 1-6 |
| Top coat (in formula no.) | 2-2 | 2-3 | 2-1 |
| Appearance before wetting in water | Homogeneous and glossy | Homogeneous and glossy | Homogeneous and glossy |
| Lubricity before coating/COF_1 | 1.37 | 1.42 | 1.39 |
| Lubricity after coating/COF_2 | 0.057 | 0.052 | 0.067 |
| Lubricity after dry-out test/COF_3 | 0.075 | 0.13 | 0.75 |

Table 5 shows that a lubricious and stable coating for latex substrates can be achieved through various combinations of base and top coating layers.

To determine the effect of wetting and drying on the lubricity of the coatings, the coated latex catheter samples were wetted for 1 minute in water and left to dry in air for 10 minutes. Following which, the friction values (COF) were measured again without allowing the samples to come into contact with water. The gripper was wiped dry after each test.

Table 5 compares the COF values of the three latex samples before the dry-out test and after the dry-out test. As depicted in Table 5, samples 11 and 12 retain lubricity after the dry out test, while the surface of sample 13 is almost dry, so it provides a much higher COF in comparison to its initial COF before wetting and drying.

Example 6—Application of Coating to Different Materials

As the coating formulae used here are intended as a platform, which can be tuned to enable the coating of a wide variety of materials with totally different surface potentials. To demonstrate this potential, various materials were coated as shown in Table 6 using General Procedure 1.

TABLE 6

| | Material used | | | | | | | | | |
| --- | --- | --- | --- | --- | --- | --- | --- | --- | --- | --- |
| | PVC | PU | PEBAX™ | Latex | Silicone | Nylon | PE | FEP | PP | Metal |
| Base coat | 1-4 | 1-4 | 1-4 | 1-6 | 1-7 | 1-4 | 1-7 | 1-7 | 1-7 | 1-5 |
| Top coat | 2-2 | 2-2 | 2-3 | 2-2 | 2-2 | 2-2 | 2-2 | 2-2 | 2-3 | 2-3 |

Figure 5:
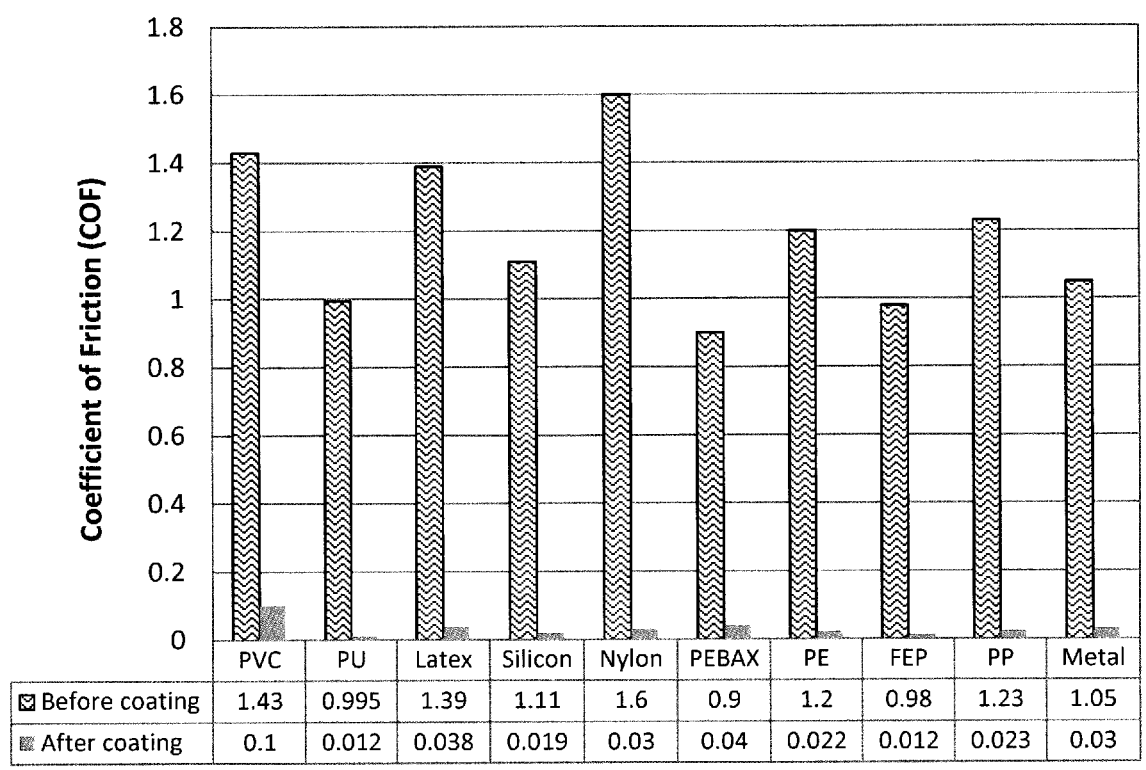
FIG. 5 depicts a comparison of the friction coefficients for different materials before and after lubricious coating.

The samples were examined and tested for lubricity, and the COF values are depicted in FIG. 5, which shows that the coatings reduced the COF of the coated materials to less than 5% of the original COF value of the uncoated materials.

Example 7—Coating on PP, FEP and Silicone

If base coating adhesion and wetting is good enough, pre-treatment can be removed. As shown in Table 8, the FEP sample was coated with three different types of base coat formula 1-4, 1-7 and base coating from a coating solution supplier. If without plasma treatment, no stable coating can be achieved by using base coat 1-4 and the coating solution ComfortCoat™. Only after plasma treatment, a homogenous and stable coating can be achieved as shown in Table 8. The comparison between samples 14 and 15 indicate that if the adhesion promoter is tuned to be more hydrophobic, then plasma pretreatment is not necessary. The coating on samples 14, 18 and 19 was found to be homogenous, stable and lubricious, as shown in Table 7.

TABLE 7

| Sample No. | 14 | 15 | 16 | 17 | 18 | 19 |
|---|---|---|---|---|---|---|
| Material | FEP | FEP | FEP | FEP | PP | Silicone |
| Pretreatment | none | plasma | none | plasma | none | none |
| Base coat (in formula no.) | 1-7 | 1-4 | ComfortCoat ™ | Company A | 1-7 | 1-7 |
| Top coat (in formula no.) | 2-2 | 2-2 | ComfortCoat ™ | Company A | 2-2 | 2-2 |
| Appearance before wetting in water | Homogeneous and glossy | Homogeneous and glossy | Coating drop off upon first rub | Homogeneous and glossy | Homogeneous and glossy | Homogeneous and glossy |
| COF before coating | 1.25 | 1.31 | 1.31 | 1.27 | 1.15 | 1.90 |
| COF after coating | 0.03 | 0.04 | — | 0.05 | 0.03 | 0.04 |

Example 8—Molecular Weight of Top Coat Monomer/Curable Polymer on Particulate Release The crosslinking network formed by UV curing plays an important role in particulate releasing control. Copolymer PVP-PEG with acrylate functional groups (PVP-PEG-AA) was synthesized (see above). The percentage of the free acrylate groups can be tuned by changing the ratio between PVP and PEGMA (i.e. the amount of free hydroxyl groups) or changing the amount of acryloyl chloride during the modification of PVP-PEG (the capping of free hydroxyl groups). The resulting PVP-PEG-AA has a multiple number of curable groups and thus can be UV cured to form a hydrophilic coating layer.

As demonstrated earlier, the base coating and top coating formula in Table 8 were applied on PTCA catheter to achieve a homogeneous, lubricous and mechanically stable coating. The COF values of sample 20 are lower than 95% of uncoated device. The coated samples were further examined for its particulate release. As shown in Table 8, samples 20 and 21 have very low counts of particulates that are greater than 10 μm and particulates that are greater than 25 μm present as compared to sample 22. In general, monomers with lower molecular weight form a tight network due to higher crosslinking density. As a result, a tighter network may reduce migration or movement of PVP from the coating into outer environment. However, the high particulate release from sample 22 suggests that even though PVP polymer interpenetrates into a tightly-crosslinked network in this case, the network could not stop PVP polymer migration from the network. On the other hand, for the same design, a tighter polymer network did give lower particulate counts as compared samples 20 with 21.

TABLE 8

| | Sample No. | | |
|---|---|---|---|
| | 20 | 21 | 22 |
| Base coat | 1-4 | 1-4 | 1-4 |
| Top coat | 2-3 | 2-4 | 2-1 |
| COF after coating | 0.043 | 0.025 | 0.03 |
| Particulate counts >10 μm | 216 | 325 | 467 |
| Particulate counts >25 μm | 8 | 11 | 29 |

The invention claimed is:

1. An adhesion promoting coating formulation for applying to a substrate material, comprising:
   a polymeric adhesion promoter;
   a first monomeric or polymeric crosslinking agent;
   a photoinitiator; and
   a solvent, wherein
   the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group; and
   when the polymeric adhesion promoter is a hydrophilic polymer comprising hydrophilic functional groups, where from 10% to 100% of the hydrophilic functional groups are capped with a hydrophobic functional group, the hydrophilic polymer comprising hydrophilic functional groups is one or more of the group selected from polyethylenimine (PEI), polyacrylamide (PAM), polysaccharide, and poly(vinyl alcohol) (PVA), and
   the hydrophobic functional group caps one or two hydrophilic functional groups and is selected from one or more of methylene (CH2), methyl (CH3), ethylene (CHCH3), ethyl (CH2CH3), C3-6 alkyl, and C3-6 alkylene, where the latter two groups are unsubstituted or substituted by a hydroxyl group.

2. An adhesion promoting coating for forming a base coating layer on a substrate material onto which a lubricious top layer coating can be formed, comprising:
   a polymeric adhesion promoter; and
   a first crosslinked polymeric matrix formed by a first monomeric or polymeric crosslinking agent, wherein the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group; and when the polymeric adhesion promoter is a hydrophilic polymer comprising hydrophilic functional groups, where from 10% to 100% of the hydrophilic functional groups are capped with a hydrophobic functional group, the hydrophilic polymer comprising hydrophilic functional groups is one or more of the group selected from polyethylenimine (PEI), polyacrylamide (PAM), polysaccharide, and poly(vinyl alcohol) (PVA), and the hydrophobic functional group caps one or two hydrophilic functional groups and is selected from one or more of methylene (CH2), methyl (CH3), ethylene (CHCH3), ethyl (CH2CH3), C3-6 alkyl, and C3-6 alkylene, where the latter two groups are unsubstituted or substituted by a hydroxyl group.

3. The adhesion promoting coating formulation of claim 1, wherein, when the polymeric adhesion promoter is a block copolymer, the hydrophilic block is chosen from one or more of the group selected from polysaccharide (such as chitosan), poly(vinyl alcohol) (PVA), polymethacrylic acid, poly(ethylene glycol) (PEG), polyacrylamide (PAM), poly(-oxazoline), and polyethylenimine (PEI), and the hydrophobic block is chosen from one or more of the group selected from polystyrene (PS), polybutadiene (PB), polyisoprene (PI), poly(methyl methacrylate) (PMMA), poly(methylacrylate) (PMA), poly(propylene oxide) (PPO), poly(hydroxyethylmethacrylate) (PHEMA), poly(vinyl ether) (PVE), poly(vinyl methyl ether) (PVME), poly(vinyl butyl ether) (PVBE), polyimide and poly(dimethylsiloxane) (PDMS), poly(N-isopropylacrylamide) (PNIPAM).

4. The adhesion promoting coating formulation of claim 1, wherein, when the polymeric adhesion promoter is a hydrophilic polymer comprising hydrophilic functional groups, where from 10% to 100% of the hydrophilic functional groups are capped with a hydrophobic functional group, the hydrophilic polymer comprising hydrophilic functional groups is one or more of the group selected from polyethylenimine (PEI), polyacrylamide (PAM), polysaccharide, and poly(vinyl alcohol) (PVA), and the hydrophobic functional group caps one or two hydrophilic functional groups and is selected from one or more of methylene ($CH_2$), methyl ($CH_3$), ethylene ($CHCH_3$), ethyl ($CH_2CH_3$), $C_{3-6}$ alkyl, and $C_{3-6}$ alkylene (e.g. $CH(CH_2)_2CH_3$), where the latter two groups are unsubstituted or substituted by a hydroxyl group.

5. The adhesion promoting coating formulation of claim 1, wherein from 25% to 100% of the hydrophilic functional groups are capped with a hydrophobic functional group.

6. A kit of parts for forming a lubricious coating on a substrate surface in need thereof, said coating comprising an adhesion promoting coating layer directly on the surface of the substrate and a lubricious coating layer on the adhesion promoting coating layer, the kit comprising:

(a) an adhesion promoting coating formulation as described in claim 1; and (b) a lubricious coating formulation comprising:
a solvent;
an initiator; and at least one hydrophilic curable polymer having at least two curable functional groups or at least one hydrophilic curable polymer with at least one curable functional group and a monomeric or polymeric crosslinking agent with at least two curable functional groups.

7. A lubricious coating for coating a substrate surface in need thereof, comprising:

an adhesion promoting coating layer for forming a base coating layer on a substrate material onto which a lubricious top layer coating can be formed, comprising:
a polymeric adhesion promoter;
a first crosslinked polymeric matrix formed by a first monomeric or polymeric crosslinking agent, wherein the polymeric adhesion promoter is a block copolymer comprising hydrophobic and hydrophilic polymer blocks and/or a hydrophilic polymer comprising hydrophilic functional groups, where from 10% to 100% of the hydrophilic functional groups are capped with a hydrophobic functional group: and when the polymeric adhesion promoter is a hydrophilic polymer comprising hydrophilic functional groups, where from 10% to 100% of the hydrophilic functional groups are capped with a hydrophobic functional group, the hydrophilic polymer comprising hydrophilic functional groups is one or more of the group selected from polyethylenimine (PEI), polyacrylamide (PAM), polysaccharide, and poly(vinyl alcohol) (PVA), and the hydrophobic functional group caps one or two hydrophilic functional groups and is selected from one or more of methylene (CH2), methyl (CH3), ethylene (CHCH3), ethyl (CH2CH3), C3-6 alkyl, and C3-6 alkylene, where the latter two groups are unsubstituted or substituted by a hydroxyl group; and a lubricious coating layer comprising a second crosslinked polymer matrix formed by:

(a) curing at least one hydrophilic curable polymer having at least two curable functional groups with itself; or (b) curing of at least one hydrophilic curable polymer having at least one curable functional group in combination with a monomeric or polymeric crosslinking agent having at least two curable functional groups, where the monomeric or polymeric crosslinking agent has a molecular weight of from 200 to 1000 Daltons.

8. The lubricious coating of claim 7, wherein:
(a) the polymeric adhesion promoter and the first crosslinked polymeric matrix are physically bound together.

9. A process to coat the whole or part of an article with a lubricious coating, comprising the steps of:

(a) providing an article with at least one surface to be coated;

(b) coating the at least one surface with an adhesion promoting coating formulation as described in claim 1 to form a base-coated article;

(c) subjecting the base-coated article to curing to form a cured, base-coated article;

(d) coating the cured, base-coated article with a lubricious coating formulation as described in claim 6 to provide an uncured lubricious-coated article; and (e) subjecting the uncured lubricious-coated article to curing to form a lubricious-coated article.

10. The process according to claim 9, wherein the curing in steps (c) and (e) are conducted using ultraviolet curing conditions.

11. The process according to claim 9, wherein the curing step (c) is conducted for a period of time $t_1$ that allows for crosslinking to occur between the base coat later and the top coat layer in step (e), such that the resulting coating on the coated article is stable over twenty cycles in a lubricity test.

12. The lubricious coating of claim 8, wherein the polymeric adhesion promoter and the first crosslinked polymeric matrix are physically bound together to form an interpenetrating network.

13. The lubricious coating of claim 7, wherein the adhesion promoting coating layer and the lubricious coating layer are interconnected by crosslinking between the first and second crosslinked polymer matrices.

14. The lubricious coating of claim 7, wherein the combined coating thickness of the adhesion promoting coating layer and the lubricious coating layer in a dry state is from 50 nm to 50 µm.

15. The lubricious coating of claim 14, wherein the combined coating thickness of the adhesion promoting coating layer and the lubricious coating layer in a dry state is from 0.5 µm to 20 µm.

16. The lubricious coating of claim 7, wherein the lubricious coating is on a substrate surface, where the surface is made from one or more of the group consisting of a metal, or a polymer, optionally wherein the polymer is one or more of polyurethane, polyvinyl chloride, latex, pebax, nylon, polypropylene, polyethylene, fluorinated ethylene propylene, poly(ethene-co-tetrafluoroethene), polytetrafluoroethylene and silicone elastomers.

17. The lubricious coating of claim 7, wherein in the adhesion promoting coating layer, the adhesion promoter is present in an amount of equal to or less than 80 wt % of the adhesion promoting coating layer.

18. The lubricious coating of claim 17, wherein in the adhesion promoting coating layer, the adhesion promoter is present in an amount from 15 wt % to 65 wt % of the adhesion promoting coating layer.

19. The lubricious coating of claim 7, wherein in the adhesion promoting coating layer, the first crosslinked polymeric matrix is present in an amount of from 20 wt % to 85 wt %.

20. The lubricious coating of claim 7, wherein in the lubricious coating layer, when the second crosslinked polymer matrix is formed by curing at least one hydrophilic curable polymer having at least one curable functional group in combination with a monomeric or polymeric crosslinking agent having at least two curable functional groups, the at least one hydrophilic curable polymer having at least one curable functional group is present in an amount of above 35 wt %, the monomeric or polymeric crosslinking agent is present in an amount of 0.5 wt % to 70 wt %.

21. The lubricious coating layer of claim 7, wherein the functional group(s) on the at least one hydrophilic curable polymer having at least one or two curable functional groups is selected from one or more of the group consisting of acrylate and methacrylate.

22. The lubricious coating layer of claim 7, wherein the at least one hydrophilic curable polymer having at least one or two curable functional groups is selected from one or more of the group consisting of polyethers, polyvinylpyrrolidone (PVP), polyesters, polyvinyl alcohols, polysaccharides, hyaluronic acid, alginates, gelatin, chitin, and copolymers thereof, optionally wherein the at least one hydrophilic curable polymer having at least one or two curable functional groups is selected from one or more of the group consisting of poly(ethylene glycol) (PEG), poly(propylene glycol) (PPG), PEG-co-PPG, PEG-co-PPG-co-PEG, poly(ε-caprolactone), polylactide, poly(lactide-co-glycolide), poly (ε-caprolactone-b-ethylene glycol-b-ε-caprolactone), poly (lactide-b-ethyleneglycol-b-lactide), poly[(lactide-co-glycolide)-b-ethylene glycol-b-(lactide-co-glycolide)], polyvinylpyrrolidone (PVP), and PVP-co-PEG, optionally wherein the least one or two curable functional groups is acrylate.

23. The lubricious coating layer of claim 7, wherein:
(a) the monomeric or polymeric crosslinking agent is selected from the group consisting of dipentaerythritol hexaacrylate, polybutadiene diacrylate, 1,10-decanediol diacrylate, tricyclodecane dimethanol diacrylate, dipropyleneglycol diacrylate, neopentylglycol propoxylate diacrylate, ditrimethylol propanetetraacrylate, ethoxylated pentaerythritol tetraacrylate, ethoxylated trimethylol propanetriacrylate, ethoxylated isocyanuric acid triacrylate, tripropylene glycoldiacrylate, pentaerythritol triacrylate, 1,10-dodecanediol dimethacrylate, ethoxylated cyclohexanedimethanol di(meth) acrylate, 2-hydroxy 1-3-dimethacryloxy propane, ethoxylated bisphenol A di(meth)acrylate, bisphenol A epoxy acrylate, diethylene glycol dimethacrylate, ethyleneglycol dimethacrylate, tricyclodecane dimethanol dimethacrylate, triethyleneglycol dimethacrylate, PEG diacrylate or PEG methacrylate, optionally wherein the monomeric crosslinker does not contain an amide group; and/or
(b) the at least one hydrophilic curable polymer having at least one or two curable functional groups has a number average molecular weight of from 20,000 to 200,000 Daltons; and/or
(c) the at least one hydrophilic curable polymer having at least one or two curable functional groups is a nonionic linear, branched or crosslinked hydrophilic polymer; and/or
(d) the solvent may be water and/or an organic solvent, optionally wherein the organic solvent is selected from one or more of the group consisting of alcohols.

* * * * *